United States Patent [19]

Williamson

[11] 4,120,192
[45] Oct. 17, 1978

[54] GAS SAMPLING APPARATUS

[76] Inventor: Lionel Herbert Williamson, 2292 Weston Rd., Apt. 806, Weston, Ontario, M9N 1Z2, Canada

[21] Appl. No.: 807,475

[22] Filed: Jun. 17, 1977

[51] Int. Cl.² .............................................. G01N 7/04
[52] U.S. Cl. ...................................................... 73/19
[58] Field of Search ........................ 73/19, 61 R, 64.2

[56] References Cited

U.S. PATENT DOCUMENTS

| 3,673,853 | 7/1972 | Griswold et al. ......................... 73/19 |
| 3,740,320 | 6/1973 | Arthur ................................. 73/19 X |

FOREIGN PATENT DOCUMENTS 1,051,029  2/1959  Fed. Rep. of Germany .............. 73/19
2,142,865  3/1972  Fed. Rep. of Germany .............. 73/19

Primary Examiner—Richard C. Queisser
Assistant Examiner—Joseph W. Roskos
Attorney, Agent, or Firm—Arne I. Fors

[57] ABSTRACT

A gas sampling method and apparatus for determining the volume of air present in carbonated liquid in bottles and cans and in process lines. The method comprises testing a predetermined quantity of liquid containing $CO_2$ gas by absorbing free $CO_2$ gas evolved from said liquid in a liquid $CO_2$-absorbent solution whereby any air is concentrated as a residual gas and subjecting said liquid $CO_2$-absorbent solution with residual gas in a confined volume under a predetermined compressive force and measuring any resulting volumetric change whereby the volume of air present can be determined.

8 Claims, 2 Drawing Figures

GAS SAMPLING APPARATUS

BACKGROUND OF THE INVENTION

This invention relates to a gas sampling apparatus and is particularly directed to a method and apparatus for determining the volume of air present in carbonated liquids such as carbonated beverages in bottles and cans during bottling or canning operations and in process lines.

The quantity of air and carbon dioxide ($CO_2$) present in carbonated beverages can be readily determined in bulk containers and in pipelines. However, the determination of these gases in liquids after packaging in bottles or cans, particularly at the high speeds encountered in existing filling machines, can be difficult and time consuming to ascertain. The presence of air in carbonated beverages, the air often being occluded in the liquid as it is loaded in the individual containers, is undesirable in that the air has a deleterious effect on carbonated beverages, such as beer, due to oxidation of beer constituents by oxygen in the air. The periodic sampling of bottles and cans filled with carbonated beverages for determining the quantity of air entrained thus is important for maintaining proper quality control and consistency of product.

STATEMENT OF INVENTION

The method and apparatus of the present invention is directed to the measurement of air in carbonated beverages in process lines and in bottles or cans moving through a packaging system at high speed. More particularly, the method of my invention for determining the quantity of air present in a liquid containing dissolved $CO_2$ comprises the steps of: introducing a predetermined quantity of said liquid to a sampling system; agitating said liquid, if necessary, for evolution of free $CO_2$ and other gases present at atmospheric pressure; preferentially absorbing said free $CO_2$ gas in a liquid $CO_2$—absorbent solution contained in said system whereby any air present in said gas is concentrated as a residual gas in said liquid $CO_2$—absorbent solution; subjecting said liquid $CO_2$—absorbent solution and said residual gas in a confined volume to a predetermined compressive force and measuring any resulting volumetric change whereby the volume of air present can be determined.

The method of my invention finds particular utility in determining the amount of air present in bottles and cans of beer and the like containers of carbonated beverages. The contents of the containers preferably are agitated by shaking or ultrasonics to accelerate the liberation of gases. The absorption of $CO_2$ gas in the liquid solution, such as, for example, an aqueous solution of caustic soda, preferably is accelerated by stirring the liquid solution by an impeller or by subjecting rising bubbles of the gas to a countercurrent downward flow of the liquid $CO_2$—absorbent solution.

The apparatus for carrying out the foregoing method comprises in general means defining a confined volume, means for introducing a liquid solution capable of absorbing $CO_2$ gas to said confined volume filling said confined volume, means for sampling a liquid containing $CO_2$ gas, means, if necessary, for agitating said liquid containing $CO_2$ gas for evolution of said $CO_2$ gas whereby said $CO_2$ gas and other gases present pass into said confined volume through the sampling means and whereby said $CO_2$ gas is absorbed in the liquid $CO_2$—absorbent solution and any air is concentrated as a residual gas, and means in communication with said confined volume for compressing the liquid $CO_2$—absorbent solution and any residual gases and for measuring the amount of volumetric change whereby the volume of air present can be determined.

In a preferred embodiment of my apparatus, said means defining a confined volume comprises a vessel having an inlet at the bottom thereof in communication with the sampling means, an inlet at the top thereof for introducing a downward flow of said liquid $CO_2$—absorbent solution, and an outlet in proximity to the bottom thereof for discharging said liquid $CO_2$—absorbent solution, said means for introducing a liquid $CO_2$—absorbent solution to said vessel at the top inlet comprising a pump for feeding said liquid $CO_2$—absorbent solution into the top of the vessel at a velocity greater than the terminal velocity of rising gas bubbles but at a velocity within the vessel slower than the said terminal velocity of said air bubbles whereby said bubbles are collected or in proximity to the said top inlet.

Said means for compressing the liquid solution and residual gases therein comprises valving means for confining said liquid $CO_2$—absorbent solution and residual gases in a confined chamber of predetermined volume and a piston mounted in a cylinder in communication with said chamber having actuating means for exerting a predetermined compressive force on said liquid $CO_2$—absorbent solution for compression of any residual gases and means for measuring the volumetric change thereof.

BRIEF DESCRIPTION OF THE DRAWINGS

The method and apparatus of my invention will now be described with reference to the accompanying drawings in which.

DESCRIPTION OF THE PREFERRED EMBODIMENT

Figure 1:
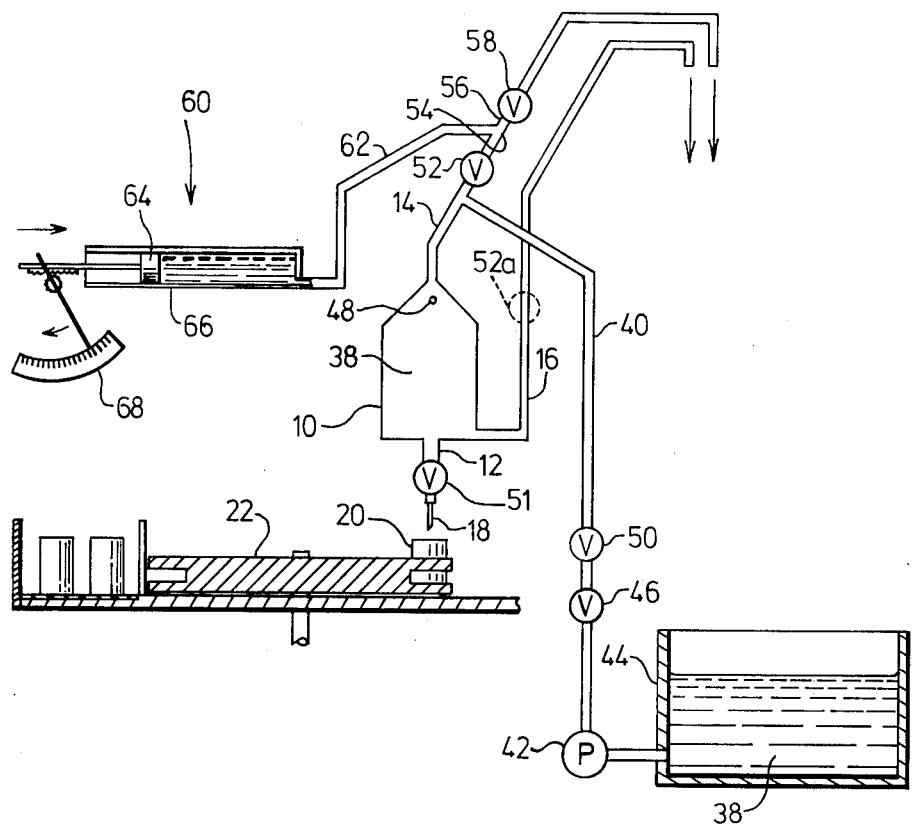
FIG. 1 is a schematic view, partly in elevation, of the system of the invention.

The apparatus illustrated comprises a vessel 10 having a bottom inlet conduit 12, top inlet conduit 14 and bottom outlet conduit 16 in communication with the interior of vessel 10. Bottom inlet conduit 12 communicates vessel 10 with sampling device 18 which is a conventional piercing device reciprocally mounted for vertical movement through the cap or top of a bottle, metal can or the like container 20 stationed as shown in FIG. 1.

Figure 2:
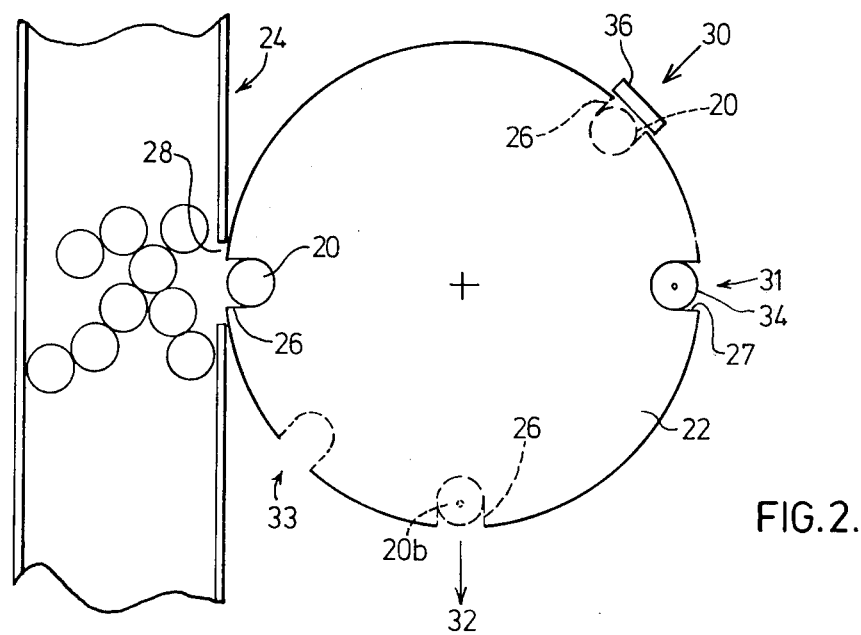
FIG. 2 is a plan view of the feeder apparatus shown in elevation in FIG. 1.

Container 20 is randomly selected from a production line by turntable 22, shown more clearly in FIG. 2, which is power driven intermittently such that container 20 crowded into peripheral cavity 26 through conveyor wall opening 28 is advanced by rotation of turntable 22, clockwise in the embodiment illustrated, to the station designated by numeral 30 where container 20, shown by broken lines, is tested. Upon completion of testing, container 20 is advanced to holding station 31 while a fresh container enters cavity 27, diametrically opposed to cavity 26, through conveyor wall opening 28. As the fresh container is advanced to testing station 30, cavity 27 having previously-tested container 34 is advanced to a holding station 33 through ejection station 32, where container 34 is discharged preparatory to entry of the fresh container 20 to turntable 22. The rotation of turntable 22 determines the speed of testing the containers and can be readily controlled by the use of timing devices in conjunction with micro-switches well known in the art.

Turntable 22 can be shaken to agitate the contents of container 20. Preferably, however, the contents of container 20 are agitated by the use of an ultrasonic transducer 36 immediately prior to and during the piercing of the container at station 30 to accelerate the liberation of gases dissolved and entrained with the carbonated beverage.

Gases rising through sampling device 18 into vessel 10 via inlet conduit 12 encounter liquid $CO_2$—absorbent solution 38 consisting of an aqueous solution of caustic soda or the like liquid capable of absorbing $CO_2$ gas. Liquid $CO_2$—absorbent solution 38 is supplied to vessel 10 through inlet conduit 14 from conduit 40 having pump 42 in series and in communication with reservoir tank 44.

Pump 42 supplies liquid $CO_2$—absorbent solution 38 under pressure to throttling valve 46 which regulates the flow of liquid $CO_2$—absorbent solution 38 downwardly through inlet conduit 14 at a velocity greater than the terminal velocity of rising gas bubbles within conduit 14 but downwardly through the increased diameter of vessel 10 at a velocity less than the said terminal velocity of rising gas bubbles such that the gas bubbles collect and coalesce at the top of vessel 10 as indicated by bubble 48.

The countercurrent flow of liquid $CO_2$—absorbent solution downward against rising gas bubbles facilitates and accelerates absorption of $CO_2$ gas in the liquid solution while preventing escape of gases through the top of vessel 10. Liquid $CO_2$— absorbent solution is discharged through bottom outlet conduit 16 to reservoir tank 44 for recycle to vessel 10 at a level higher than valve 58 to prevent draining of the system when valves 52 and 58 open due to siphoning. Recycling of liquid $CO_2$—absorbent solution 38 ensures provision of an adequate supply of solution for a considerable number of samples before necessitating replenishment. I have found that the $CO_2$ gas can be absorbed in a caustic soda solution in 5 to 10 seconds leaving residual gases normally consisting of air as a concentrate.

Upon completion of absorption of $CO_2$ gas, pump 42 is stopped with resulting cessation of flow of liquid $CO_2$—absorbent solution 38. Check valve 50 in conduit 40 prevents back-flow of liquid $CO_2$—absorbent solution into reservoir tank 44 such that the system remains filled. Valve 51 closes and valve 52 opens concurrently with shutdown of pump 42. Bubble 48 rises into conduit 14 and through open valve 52 into a chamber 54 defined by conduit 56 between closed valve 58 and valve 52. Valve 52 is closed once bubble 48 has passed through defining a confined volume in chamber 54 which is in communication with a pistoncylinder assembly 60 by conduit 62.

The piston 64 is actuated within the cylinder 66 under a predetermined compressive force, such as by a fixed deadweight thereon, to transmit and exert a known pressure on the gas bubble in chamber 54 through the medium of solution 38. The movement of piston 64 will vary directly proportional to the size of gas bubble present and a scale 68 associated with piston movement will provide a direct readout of gas volume and percentage of air present in the container tested.

A strip or circular chart electrically or pneumatically connected to piston 64 can provide a permanent record of sampling results.

Valves 52 and 58 are opened upon completion of the gas volume measurement concurrent with retraction of piston 64 and energization of pump 42 to purge gas in chamber 54, valve 58 is closed, and sampling mechanism 18 is actuated to pierce the next container 20 concurrently with opening of valve 51 when the container has been positioned therebelow to repeat the sampling cycle.

Sampling of a carbonated liquid in a pipeline by tapping a known volume of said liquid directly to vessel 10 is contemplated, together with the provision of an impeller within vessel 10 to aid mixing of liquid solution 38 with gas bubbles. Valve 52 can be located as indicated by broken lines 52a. However, the location of valve 52 as indicated is preferred in order to restrict the high pressure portion of the system to piston-cylinder assembly 60, conduit 62 and conduit 56 defining chamber 54. The high pressure components can be formed of stainless steel whereas the vessel 10 and remaining piping can be formed of glass and flexible tubing resistant to corrosion by the caustic solution.

A pressure of about 150 psig has been found satisfactory to obtain accurate volumetric measurements in chamber 54.

It will be understood of course that modifications can be made in the embodiment of the invention illustrated and described herein without departing from the scope and purview of the invention as defined by the appended claims.

What I claim as new and desire to protect by Letters Patent of the United States is:

1. A method of determining the quantity of air present in a liquid containing dissolved $CO_2$ comprising the steps of: introducing a predetermined quantity of said liquid to a sampling system, preferentially absorbing free $CO_2$ gas evolved from said predetermined quantity of liquid in a liquid $CO_2$—absorbent solution contained in said system whereby any air present in said gas is concentrated as a residual gas in said liquid $CO_2$—absorbent solution, subjecting said liquid $CO_2$—absorbent solution and residual gas in a confined volume to a predetermined compressive force and measuring the amount of any resulting volumetric change whereby the volume of air present can be determined.

2. A method as claimed in claim 1, agitating said liquid containing $CO_2$ for evolution of free $CO_2$ gas at atmospheric pressure.

3. A method as claimed in claim 2, passing said liquid $CO_2$— absorbent solution downwardly countercurrent to rising bubbles of said $CO_2$ gas and residual gas to facilitate absorption of said $CO_2$ gas in said liquid $CO_2$—absorbent solution.

4. Apparatus for determining the quantity of air present in a liquid containing dissolved $CO_2$ comprising: means defining a confined volume, means for introducing a liquid solution capable of absorbing $CO_2$ gas to said confined volume filling said confined volume, means for sampling said liquid containing $CO_2$ gas whereby free $CO_2$ gas passes into said confined volume through the sampling means and whereby said $CO_2$ gas is absorbed in the liquid $CO_2$— absorbent solution and any air is concentrated as a residual gas, and means in communication with said confined volume for compressing the liquid $CO_2$ absorbent solution and any residual gas therein and for measuring the amount of volumetric change whereby the volume of air present can be determined.

5. Apparatus as claimed in claim 4, said means defining a confined volume comprising a vessel having an inlet at the bottom thereof in communication with the sampling means, an inlet at the top thereof for introducing said liquid $CO_2$—absorbent solution, and an outlet in proximity to the bottom thereof for discharging said liquid $CO_2$—absorbent solution, said means for introducing a liquid $CO_2$—absorbent solution to said vessel comprising a pump for feeding said liquid $CO_2$—absorbent solution into the top of the vessel at a velocity greater than the terminal velocity of gas bubbles rising in said liquid $CO_2$—absorbent solution at the inlet to the vessel but slower than the terminal velocity of said air bubbles within the vessel whereby said bubbles are collected at the said inlet.

6. Apparatus as claimed in claim 5, said means for compressing the liquid $CO_2$—absorbent solution and contained air therein comprising valving means for confining said liquid $CO_2$— absorbent solution and contained residual gas in a chamber within said confined volume and a piston mounted in a cylinder in communication with said chamber having actuating means for exerting a predetermined pressure on said liquid for compression of any residual gas and means for measuring the volumetric change thereof.

7. Apparatus as claimed in claim 6, said liquid solution comprising sodium hydroxide solution.

8. Apparatus as claimed in claim 7, said valving means comprising a check valve in each of the inlets from the sampling means and the liquid solution feeding means.

* * * * *